(12) United States Patent
Piao

(10) Patent No.: US 11,234,600 B2
(45) Date of Patent: Feb. 1, 2022

(54) SYSTEM AND METHOD FOR TISSUE VISUALIZATION

(71) Applicant: THE BOARD OF REGENTS FOR OKLAHOMA STATE UNIVERSITY, Stillwater, OK (US)

(72) Inventor: Daqing Piao, Stillwater, OK (US)

(73) Assignee: THE BOARD OF REGENTS FOR OKLAHOMA STATE UNIVERSITY, Stillwater, OK (US)

( * ) Notice: Subject to any disclaimer, the term of this patent is extended or adjusted under 35 U.S.C. 154(b) by 330 days.

(21) Appl. No.: 16/035,282

(22) Filed: Jul. 13, 2018

(65) Prior Publication Data
US 2019/0014986 A1 Jan. 17, 2019

Related U.S. Application Data

(60) Provisional application No. 62/697,663, filed on Jul. 13, 2018, provisional application No. 62/532,047, filed on Jul. 13, 2017.

(51) Int. Cl.
*A61B 5/00* (2006.01)
*A61B 1/07* (2006.01)
(Continued)

(52) U.S. Cl.
CPC .............. *A61B 5/0084* (2013.01); *A61B 1/07* (2013.01); *A61B 1/3132* (2013.01);
(Continued)

(58) Field of Classification Search
CPC ..... A61B 5/743; A61B 5/0075; A61B 5/0084; A61B 1/07; A61B 1/3132;
(Continued)

(56) References Cited

U.S. PATENT DOCUMENTS

| | | | |
|---|---|---|---|
| 2008/0214940 A1* | 9/2008 | Benaron | A61B 5/415 600/478 |
| 2015/0265256 A1* | 9/2015 | Bierhoff | A61B 5/6848 600/427 |

FOREIGN PATENT DOCUMENTS

WO WO-9945838 A1 * 9/1999 ........... A61B 5/0071

OTHER PUBLICATIONS

"Real-time In Vivo Tissue Characterization with Diffuse Reflectance Spectroscopy during Transthoracic Lung Biopsy: A Clinical Feasibility Study" by J.W. Spliethoff et al. Clinical Cancer Research. vol. 22, Issue 2. pp. 357-365. Jan. 2016 (Year: 2016).*

(Continued)

*Primary Examiner* — Jason M Ip
(74) *Attorney, Agent, or Firm* — Fellers, Snider, Blankenship, Bailey & Tippens, P.C.; Terry L. Watt

(57) ABSTRACT

This invention is regarding a set of stand-alone or combined-use surgical tools and associated systems and methods for performing surgical procedures such as identifying hidden tissue anatomy and dissecting the periphery tissues. In particular, this invention describes tools and the associated systems and methods for visualizing hidden important structures such as arteries, veins, ureters, bile duct, bowel, nodules, tumors, and performing tissue cutting using energy-based instrument. The tools are to be operated stand-alone or by attaching to existing instruments used for minimally invasive surgery.

18 Claims, 5 Drawing Sheets

(51) Int. Cl.
    *G01J 3/02*           (2006.01)
    *G01J 3/42*           (2006.01)
    *A61B 1/313*         (2006.01)
    *A61B 90/30*         (2016.01)
    *A61B 90/00*         (2016.01)

(52) U.S. Cl.
    CPC ............ *A61B 5/0075* (2013.01); *A61B 5/743* (2013.01); *G01J 3/0218* (2013.01); *G01J 3/42* (2013.01); *A61B 2090/306* (2016.02); *A61B 2090/3614* (2016.02); *A61B 2090/3735* (2016.02)

(58) Field of Classification Search
    CPC ....... A61B 2090/306; A61B 2090/3614; G01J 1/0425; G01J 3/10; G01J 3/42; G01J 3/0218
    See application file for complete search history.

(56) References Cited

OTHER PUBLICATIONS

"Time-resolved spectrofluorometer for clinical tissue characterization during endoscopy" by T. Glanzmann et al. R Scientific Instruments. 70, 4067 (Year: 1999).*

\* cited by examiner

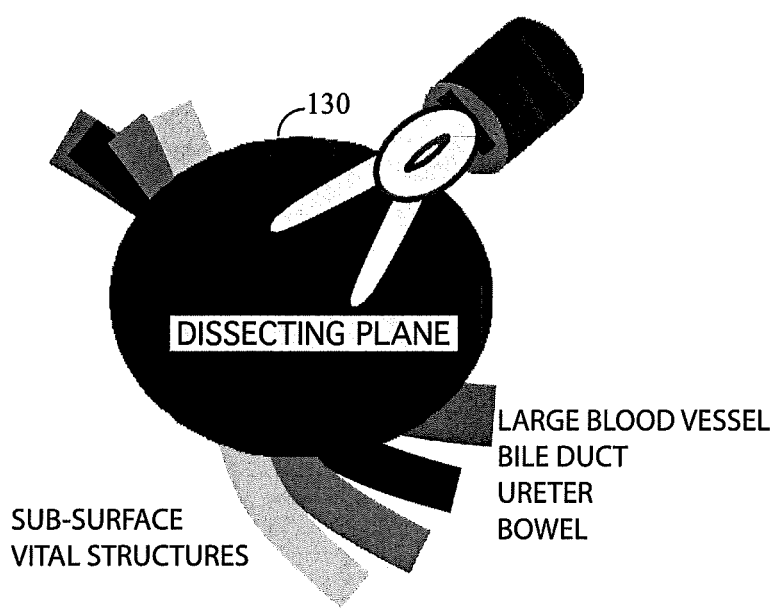
Fig. 1A
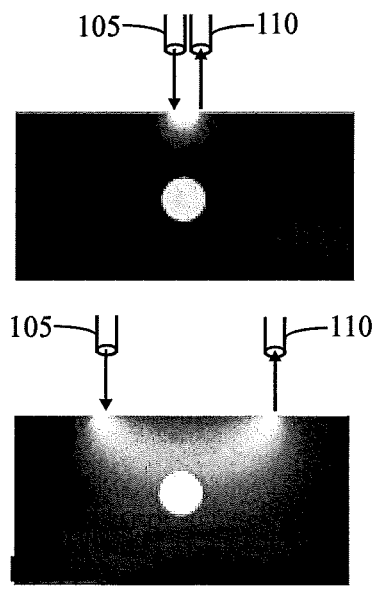
Fig. 1B
Fig. 1C
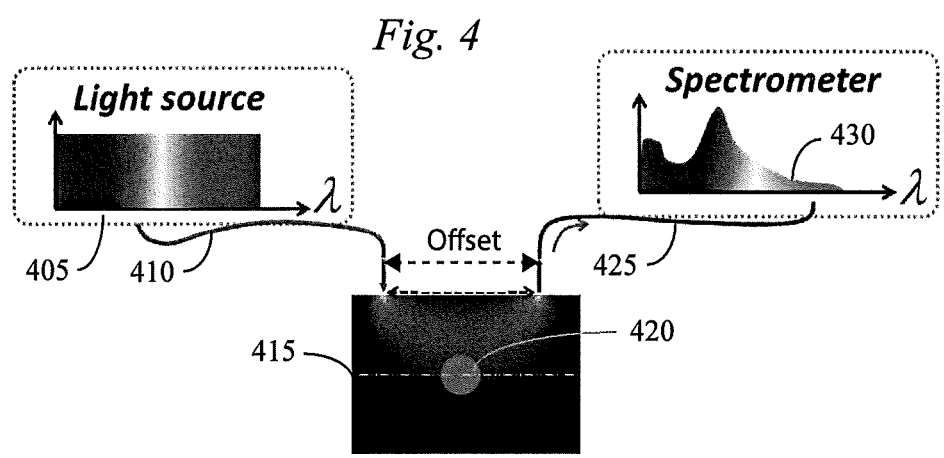
Fig. 4

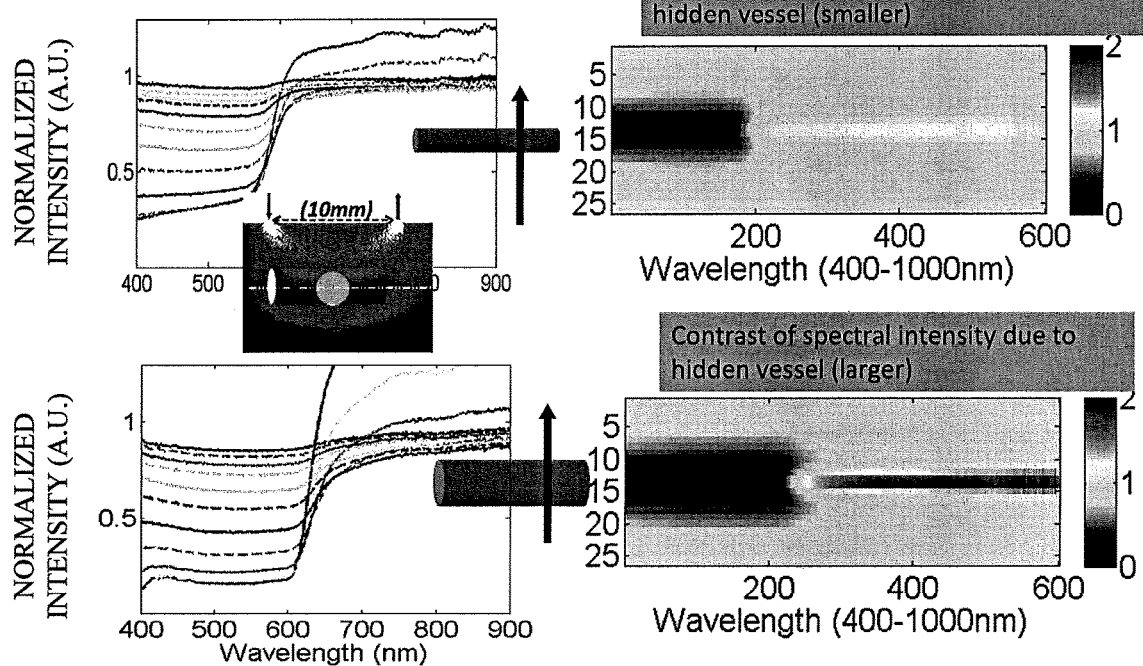
*Fig. 10*
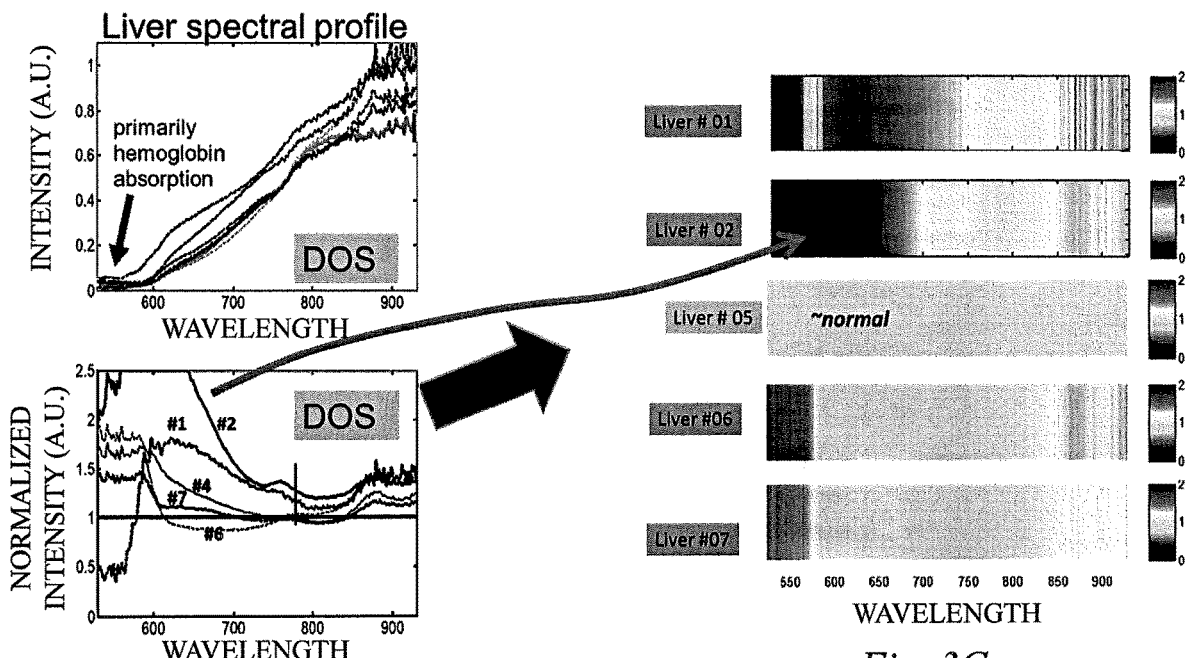
*Fig. 3A*
*Fig. 3B*
*Fig. 3C*

SYSTEM AND METHOD FOR TISSUE VISUALIZATION

CROSS REFERENCE TO RELATED APPLICATIONS

This application claims the benefit of U.S. Provisional Patent Application Ser. No. 62/532,047 filed on Jul. 13, 2017, and incorporates said provisional application by reference into this document as if fully set out at this point. This application also claims the benefit of U.S. Provisional Patent Application Ser. No. 62/697,663 filed on Jul. 13, 2018, and incorporates said provisional application by reference into this document as if fully set out at this point.

TECHNICAL FIELD

This disclosure relates generally to medical imaging devices and, more specifically, to systems and methods of tissue visualization of the sort used in pure laparoscopic, robotic-assisted laparoscopic and open procedures.

BACKGROUND

Preventing inadvertent injuries to important anatomic structures including, but not limited, to veins, arteries, ureters, bile duct, and bowel, is challenging in minimally invasive procedures due to limitations in the surgeon's ability to visualize those anatomic structures hidden below the fat or scar tissue to navigate around them. Patients who suffer inadvertent injury to any of those important anatomic structures face corrective procedures that often require not only conversion from minimally-invasive to open surgery, but also extended hospital stays which can add tens of thousands of dollars to their healthcare expenses, increased risks of nosocomial infections, and higher mortality rates which, in some cases, might be as much as 32% higher. The risk of inadvertent injury to important anatomic structures is a concern that potentially increases operative time, which in turn lengthens a patient's exposure to anesthesia, and increases overall costs. The risk of inadvertent injury to important anatomic structures becomes even greater for obese patients, because the large layer of peritoneal fat further challenges intraoperative definition of the internal anatomy that is inherently difficult for minimally invasive surgery.

Minimally invasive (e.g., pure laparoscopic or robotic-assisted laparoscopic) procedures have increasingly become the preferred surgical approach for management of several benign and malignant abdominal surgical conditions in various surgical specialties (general surgery, gynecology, and urology). Over the years, improvement in visualization and increased surgeon familiarity with laparoscopic techniques has resulted in an increased utilization of minimally invasive surgery. In patients with solid-organ malignancies, particularly urologic and gynecologic malignancies including uterine, cervical, prostate, bladder and kidney cancers, robotic laparoscopic surgery has increasingly become the surgical approach of choice.

However, when compared to open procedures, laparoscopic procedures are faced with challenges in proper identification of anatomical "danger zones" which include large arteries/veins, ureter, bowel, bile duct, etc. In contrast to traditional open surgery, identification of these areas is more difficult due to poor or absent tactile feedback from pure and robotic-assisted laparoscopic techniques respectively. Techniques that help identify these significant tubular structures underlying the tissue surfaces of dissection would have the potential to reduce iatrogenic injury, and lower operative times due to timely identification for direct enhancement of surgical outcomes.

There are recent developments of stand-alone laparoscopic probes that aim to sense specifically arterial vessels using the mechanical pressure changes due to pulsation. Some other laparoscopically applicable devices designed for identifying arterial vessel operate by detecting the variation of electrical impedance in the vessel arising from the distensile changes associated with blood pulsation. Sensing the pulsation mechanically or electrically may provide similar information to finger-like palpation used in traditional open surgery that could become very intuitive and sensitive for identifying arterial vessels. Sensing the pulsation only, however, may be ineffective for the identification of low- or non-pulsatile vessels such as veins, and other important structures including ureters, bile ducts, and bowel.

Strong and characteristic light absorption in the visible spectrum by hemoglobin in the superficial tissue that is assessable by surface reflection has been utilized for laparoscopic monitoring of tissue oxygenation during esophagostomies and measurement of renal ischemia during laparoscopic partial nephrectomy. Transmission measurement of hemoglobin absorption in tissues has also been proposed as a stand-alone device technology towards identifying blood vessels during laparoscopic procedures. A transmission measurement of light absorption could allow sensitive identification of vessel-containing tissue that is "interposed" between the two grasping jaws of a laparoscopic grasping instrument; however, tissue dissection does not always allow the surgeon to place tissue between the grasping jaws of laparoscopic instruments which would require greater than 270 degree dissection around the tissue being examined.

Many laparoscopic procedures including radical prostatectomy and partial nephrectomy requires layer-by-layer dissection of tissue planes below which important anatomic structures of tubular shape including blood vessels, ureters, and bowel may hide, as is illustrated in FIG. 1(A). One intraoperative need in dissecting the tissue is the detection of important tubular structures that underlie the dissecting plane, i.e., that are not in the direct line-of-sight between the two jaws of the dissecting instrument but are at a significant depth from the plane of dissection which is visible by the video-feed. Detecting important structures at a few millimeters below the surgical dissection plane is necessary for advanced warning of potential inadvertent injury.

As such, what is needed is a device that, when light is used for making the detection, effectively samples and will be able to detect underlying anatomic structures with an applicator probe on or near the surface of the peritoneal fat or scar tissue or, more generally, the tissue plane. Furthermore, the device should be able to produce outputs that objectively distinguish the underlying anatomic structures, be they veins, arteries, or other tubular anatomy, from peripheral tissue. Furthermore, the device should be capable of being operated by surgeons within their normal operative workflow using the same set of standard and unmodified minimally invasive operative instruments.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

One approach taught herein uses the characteristic light absorption properties in the visible/near-infrared spectrum of endogenous tissue chromophores such as hemoglobin for identification of important anatomic structures including both arterial and venous vessels.

According to one embodiment, dynamic DOS profiles are displayed in the following way or any variation of which, to constitute a two-dimensional image. One dimension of the image represents the wavelength of the spectrum acquired and the other dimension represents the time when the spectrum is acquired. The value at one pixel corresponding to a specific wavelength and a specific time is the intensity of the spectrum or any parameter originating from the spectral profile. When the dynamic DOS profiles are acquired at one fixed physical position, the resulted two-dimension image represents the changes of the DOS spectrum at that position over time. When the dynamic DOS profiles are acquired at multiple positions by moving the applicator probe manually or autonomously, the resulted two-dimension image represents the differences of the DOS spectrum at multiple positions, giving a time-series-spatially-resolved spectrogram.

By displaying the dynamic DOS profiles representing the subsurface tissue attenuation as a time-series-spatially-resolved spectrogram concurrent with the scanning (freehand or autonomous or variations of both) of the probe over the tissue area of interest, the dynamic change of the DOS intensity due to underlying anatomic structures can indicate the presence of those structures below the plane of tissue on which the applicator probe is placed. When the underlying structures contain one artery and one vein in adjacent to each other, there will be a unique pattern of gradient changes of the DOS signals when the applicator probe moves over from the artery to the vein or from the vein to the artery. These unique patterns of signal change can identify the hidden artery and vein complex. The dynamic DOS profiles can also be displayed in the following way or any variation of which, to constitute a three-dimensional image. One dimension of the image represents the wavelength of the spectrum acquired. One other dimension represents the time when the spectrum is acquired. The third dimension represents a parameter that is different from the two other dimensions but provides more tissue-specific information, such as fluorescence.

In one embodiment, the applicator-probe is designed for sliding down a widely used robotic-assisted tissue maneuvering instrument for contacting the tissue for DOS and sliding up to clear the instrument for dissection. In an embodiment, the applicator probe is "piggy-backed" to the shaft of an existing surgical instrument that is used to manipulate tissue, without making any changes to the portion of instrument that is introduced into operative subject. This variation of the method/device works by measuring underlying tissue, i.e., tissue below the dissecting plane, during a layer-by-layer dissection common to minimally invasive procedures of certain specialties, such as prostatectomy whereby the fatty or peritoneal tissue is dissected layer by layer before reaching, for example, the prostate.

An embodiment of the instant method/device will detect a variety of tissue structures that may be of tubular shape or other shapes, including blood vessels, bowel, ureter, bile ducts, etc., with optical heterogeneity due to differences in properties such as absorption, scattering, fluorescence, and polarization. The operation of this method/device does not depend upon the blood pulsation. It uses light of broad spectrum, either continuum or discrete, over the wavelength range from shorter than ultraviolet to near-infrared.

An embodiment has been tested in an open-surgery platform under general room-lighting with porcine models where the aorta and vena cava were covered by peritoneal fat. to demonstrate the in vivo feasibility of using dynamic diffuse optical spectroscopy imaging (DOSi) acquired by an applicator-probe with a non-overlapping source and detector configuration. In this particular example a 10 mm source-detector separation on the probe was used to identify hidden aorta and vena cava during freehand-scanning of the applicator-probe over the tissue plane hiding the major vessels. That being said, it should be noted that the source/detector separation is not limited to a fixed 10 mm value but might instead be varied depending on the tissue type, depth of the target structure, etc. In this test the in vivo feasibility of identifying hidden major vessels according to the dynamic changes of DOS profile during freehand-scanning of the applicator-probe over the vessel-hiding tissue area was demonstrated. This variation was based on diffuse optical spectroscopy (DOS) implemented with an applicator-probe of 10 mm source-detector separation, which sleeves on to an 8 mm shaft robotic-assisted tissue manipulating instrument, rendering a sampling depth of a few millimeters below the tissue surface. Real-time in vivo response (100-300 ms acquisition time) of broadband DOS at the 10 mm source-detector separation was acquired by an ultra-bright broadband light source. A stronger source should make the response faster.

The present embodiment of DOSi demonstrates "visualization" of the hidden major vessel structures under surgical lighting. This was done by forming an image of the dynamic changes of the frequency content of the DOS profiles as the applicator-probe is scanned (manually or autonomously) over the tissue area hiding major vessels.

One approach taught herein provides information with respect to the internal tissue structure by converting the time-series of tissue spectral information (raw spectrum and any derivatives of it) during the scanning (freehand or autonomous) of the applicator probe into a dynamically updated 2-dimensional or 3-dimensional or higher-dimensional image.

This approach can be combined, for example, with other light-based visualization, detection, and tissue manipulation methods/devices, using the same configuration of the applicator probe and the scanning (free-hand or autonomous) of the applicator probe. The applicator probe for this embodiment contains fibers or fibers combined with other optical components to conduct light to the tissue by contact or remotely.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

These and further aspects of the invention are described in detail in the following examples and accompanying drawings.

FIG. 1A contains a schematic illustration of tissue dissection using a layer-by-layer dissection technique. FIGS. 1B and 1C illustrate how the optical sampling depth can vary depending on the separation of the source and detector elements.

FIG. 2 contains an embodiment of a DOSi applicator probe that has optical fibers only or fibers combined with other optical components for shaping the light path. In this embodiment the fibers are placed within two extruded terminals.

FIG. 3A contains a tissue-specific raw DOS spectral profile. FIG. 3B contains a graphic that includes the profiles of FIG. 3A which have been normalized against a baseline profile. FIG. 3C illustrates the spectral representation of subsurface liver structures after the sensed light has been normalized according to a normal liver profile.

FIG. 4 contains a schematic that illustrates in a general way how an embodiment uses light diffused from a tissue plane to detect subsurface structures. Using the dynamically updated DOS signal to form an image that provides identification of tissue heterogeneity underlying the tissue surface upon which the probe is placed (phantom results).

FIG. 10 contains exemplary test results of tubes of 2 and 4 mm sizes with dye of a given contraptions at various depths. The image visualized the relative position changes of the tube with respect to the probe, and the different tube sizes.

DETAILED DESCRIPTION

Figure 2A:
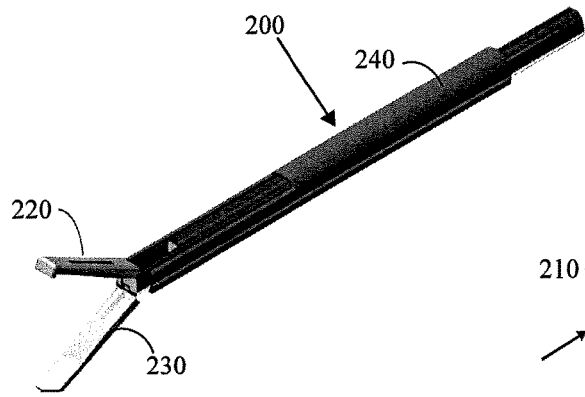
FIG. 2A illustrates a configuration where the probe is retractable along the barrel of the tissue manipulating instrument.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

Many laparoscopic procedures perform tissue dissection with a layer-by-layer dissection technique. During these procedures, important anatomic structures including large blood vessel, bile duct, ureter, and bowel below the dissecting plane are not visible to the surgeon and are difficult to detect by tactile sensations. FIG. 1A illustrates the general nature of this problem.

Various embodiments of the instant invention seek to overcome these problems by interrogating the anatomic structures below the surface of the tissue by using an improved diffuse optical spectroscopy (DOS) in a laparoscopically compatible device. In brief, an embodiment provides a method of converting conventional DOS signals into an imaging visualization tool, thereby making it possible to detect sub-surface anatomic structures (e.g., a tubular shape being one of the most common cases) of a few millimeters in diameter and at a depth of up to 1 cm in some variations. This can provide intraoperative assistance to the surgeon through identification of these important anatomic structures (potential surgical danger zones) without interrupting the dissection workflow.

According to an embodiment, by assessing the tissue absorption light spectrum using a diffusely propagated light source, compositions of spectrally significant and biologically important chromophores, such as hemoglobin, melanin, water and fat, in the tissue volume of diffuse photon propagation can be detected by DOS. By evaluating the scattering spectral variation of bulk tissue, morphological changes at microscopic levels such as formation of lipid droplets (e.g., Piao D., et al., 2015, "In vivo assessment of diet-induced rat hepatic steatosis development by percutaneous single-fiber spectroscopy detects scattering spectral changes due to fatty infiltration", *J Biomed Opt.;* 20 117002, the disclosure of which is incorporated herein by reference as if fully set out at this point) and disintegration of subcellular structures due to malignancy in the tissue volume of photon propagation may be detected by DOS.

Depth sensitivity, as is generally indicated by the examples of FIGS. 1B and 1C, is associated with the distance between the light source 140 and detector 150 when they are placed on the tissue surface 130 by in-contact or off-contact configurations. For a tissue content that has optical heterogeneity with respect to the background bulky tissue, diffuse optical spectroscopy can detect the existence of the tissue heterogeneity at a relevant source-detector separation rendering a sufficient sampling depth Note that, for purposes of the discussion that follows, the source-detector separation will be referred to as "SDS". Longer SDS makes sampling deeper tissue heterogeneity possible, at the likely cost of weaker signals requiring a stronger broadband source or longer time for spectral data acquisition.

Turning next to certain aspects of an embodiment, FIG. 4 provides insight into some aspects of a current approach. As is generally indicated there, a light source, preferably a broad-band light source, with a spectral frequency distribution represented schematically by spectrum 405, will be transmitted to the target tissue 415 with the aim of detecting an anomalous structure 420 therein. The preferred transmission mode is via optical fiber 410 or optics for remote projection. Offset from the source fiber 410 by a predetermined amount (the SDS) is the terminus of a detector fiber 425 which is also in contact or off-contact by remote projection with the target tissue 415.

In operation, after the light source is activated the terminus of the detector fiber 425 senses the diffuse scattered light that is reflected from the interior of the tissue 415 and transmits that signal to an optical spectrometer which produces a representation of the spectral content 430 of the sensed light signal. Changes in the spectral characteristics of the received signal 430 as compared with that of the spectrum of the source light 405 can then be used to locate anomalous structures within the target tissue 415. In some embodiments the data are taken at the spectrometer using an exposure time of 100 ms to 300 ms. The exposure time may depend upon the intensity of the light source. That translates to each spectrum being displayed at a rate of 1/exposure time. Ideally, with a very strong source and very sensitive spectrometer, it should be possible to obtain 200 exposures refreshed at a video display or refresh rate, so the targeted exposure time of the spectrometer could be 1 ms, or a sampling rate of 1000 full spectra per second in some embodiments. Of course, those of ordinary skill in the art will readily be able to modify these timing values to suit a particular situation.

Note that when the terms "spectrometer" or "optical spectrometer" are used herein, those terms should be broadly construed to include dedicated optical spectrometers as well as computers (to include desktop and laptop computers and handheld devices such as smart phones, tablet computers, etc.) that can be adapted to receive the light signal, digitize it (e.g., using a digital camera or other device with, e.g., a CCD), and numerically convert it to an amplitude spectrum. Further, note that although the spectrum 405 is shown as being flat that was only done as an illustration and the actual spectral signature of the source light could be arbitrarily different based on the needs of the particular application. Finally, and as has been previously discussed in connection with FIGS. 1B and 1C, the offset of the source fiber terminus from the detector fiber terminus is a parameter that can be varied in order to adjust the depth that is being imaged.

One approach to implementing an embodiment is to configure it so that it is piggy-backed to an existing tissue-manipulating instrument which would not require any changes to the physical structure of the tissue-manipulating instrument.

Figure 2B:
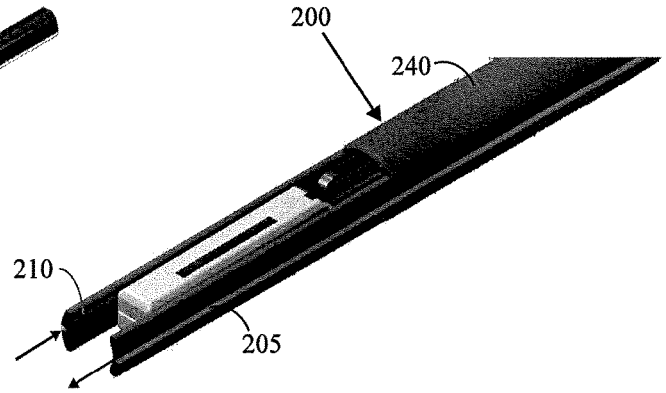
FIG. 2B illustrates the same configuration when the probe is extended to make tissue contact or measurement.

FIG. 2 illustrates one such approach. According to a first embodiment, the applicator probe 200 containing spaced apart optical fibers 205 and 210 or fibers combined with other optical components for directing the light path can be attached to an existing tissue-manipulating instrument is shown in FIG. 2. In FIG. 2B, the termini of the fibers 205 and 210 have been extended relative to the barrel 240 of the probe 200 by retracting the jaws 220 and 230 to expose them. This retraction allows the termini of the optical fibers 205 and 210 to simultaneously come into optical contact with the planar surface of the tissue that is to be interrogated. By way of comparison, in FIG. 2A the jaws 205 and 210 have been extended. Note that in this particular arrangement the optical fibers 205 and 210 are situated within grooves that run longitudinally along the length of the probe 200. This might be done for several reasons but one reason is to make the barrel 240 of the probe 200 easier to grasp and to protect the coating of the fibers 205/210 from abrasion.

Note that, for purposes of the instant disclosure, if the imaged tissue is described as having a "planar surface" that term should be broadly construed to include any sort of surface, whether flat or not, that is suitable to have the termini of the source 205 and detector 210 optical fibers both placed into contact with the same surface of the tissue at the same time.

In the embodiment of FIG. 2, the imaging components 205 and 210 are attached to the shaft of a tissue-manipulating instrument 200 by a structure that allows for sliding or snapping. The imaging components 205 and 210 may have one, two or multiple fibers each, without or with optics placed at any positions on the probe 200. The probe 200 may be brought into contact with tissue manually or it could be operated remotely (e.g., optics on the fiber could allow for a remote operation via, for example, robotic or computer assisted surgery).

Continuing with the embodiment of FIG. 2, the fibers 205 and 210 can be placed with their line-of-sight blocked by the shaft of the instrument 200 or the holding structure in the configurations shown in FIGS. 2A and 2B. The fibers 205 and 210 can be attached to the shaft 240 (but preferably not to the jaws 220 and 230 as with some prior art devices), and moved along the shaft 240 of the probe 200 in order to take tissue measurement or moved away from the terminus when the jaws 220 and 230 are in use.

Other design configurations are certainly possible. In brief, any design that allows the optical conductors (source and detector) to be simultaneously brought into proximity with the planar surface of the tissue that is to be interrogated, without or with other optical components attached thereto, and that can direct light from a light source placed outside of the body to tissue planes of dissection and capture the light being emitted from the tissue plane of dissection to a detector placed outside of the body would potentially be acceptable if the returning optical signals are processed as disclosed herein.

Note also that, unlike the prior art, in the preferred arrangement the termini of the source 205 and detector 210 are configured so that they can be made to simultaneously come into contact with or otherwise illuminate the same side of a planar surface of the tissue that is to be imaged. This is one way this embodiment differs from prior art approaches which situate a source on one side of a subject tissue and a detector on the other side and which rely on the attenuation of the transmitted or propagated light signal in order to form an image. As a consequence, since the source and detector termini of the instant embodiment are simultaneously placed in contact with or otherwise illuminate the same surface of the tissue, the resulting signal that is received at the detector is based on light that has diffusely propagated through the medium underneath.

Exemplary System/Device that Uses the Applicator Probe Piggy-Backed to the Shaft of a Tissue-Manipulating Instrument Referring again to the embodiment as shown in FIG. 4, one variation of the inventive system can use one or multiple light source units. If multiple light sources are used they might be combined before transmitting them down a single fiber optic line or each might be conveyed to the tissue surface in separate lines. Each light source might have a continuous spectrum or discrete spectral peaks and could be sourced a single or multiple light emitting elements. The spectrum of the light source in one embodiment covers from about ~300 nm to ~2 um but, of course, the range of light frequencies used might be broader or narrower than this depending on the needs of the particular imaging task. Those of ordinary skill in the art will readily be able to adjust this range to operate according to this embodiment of the invention. In operation, the detector might be comprised of a single optical fiber terminus or multiple detectors. Either way, the detector(s) then captures the light signal from the tissue which is subsequently resolved into different wavelengths as described below.

FIGS. 6 to 9 contain test results for an embodiment. These figures illustrate how the frequency of the detected light source can be used to detect subsurface heterogeneities in certain circumstances. In each of FIGS. 6 to 9 figures, the lateral axis is the wavelength of the detected diffuse light and the vertical axis is the relative position of the subsurface structure relative to the center of the probe, with "10" representing the situation where the probe was directly above the hidden structure which is a tube in this example. The shade in each strip chart represents the intensity of the received light at the frequency indicated. Operationally, the light was activated and its spectrum analyzed. The tube was then moved laterally with respect to the probe. Thus, each strip chart may be thought of as the result of a freehand movement of a probe above the structure indicated. As is indicated, the frequency content of the received signal varies as a function of the depth of the target, the optical characteristics of the target, and the position of the target relative to the probe.

Figure 6:
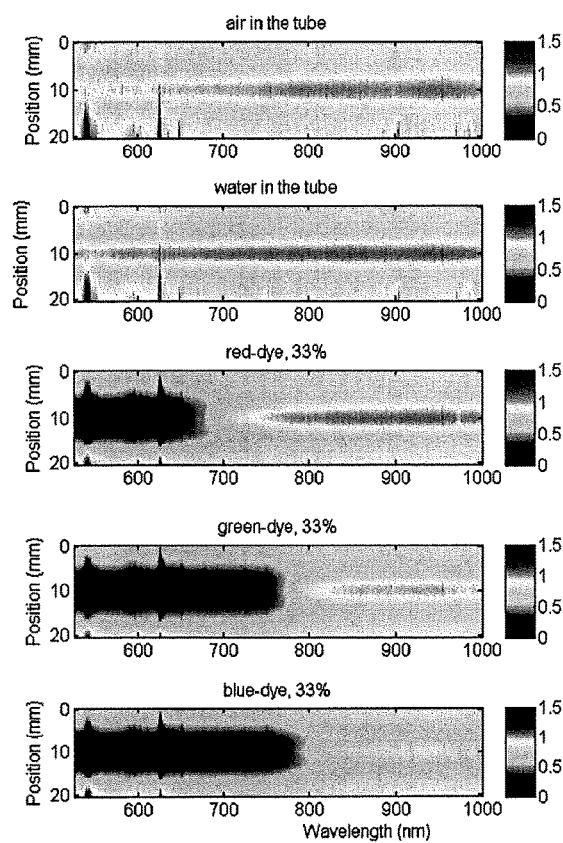
FIG. 6 contains examples of different contents in the 4 mm tube with the top surface hidden 2 mm below the medium surface/probe. The tube was moved laterally with respect to the probe, i.e., the position at 10 mm corresponds to the tube position directly below the probe.

Turning first to FIG. 6, the structure is a 4 mm tube with the top surface hidden 2 mm below the medium surface/probe. The tube was moved laterally with respect to the probe. As indicated previously, position 10 mm corresponds to the tube position directly below the probe). By way of explanation, this figure shows that this embodiment of the imaging method can detect the presence of a tubular structure below the surface of the probe plane. This figure also shows that contents of air and water are differentiated from the contents of dyes. The dyes mimic blood vessels, and the air/water-filled tubes represent structures such as bowel and ureter. The results show that the invention can in principle differentiate the blood vessel and bowel/ureter, all of which are important to detect during minimally invasive procedures)

Figure 7:
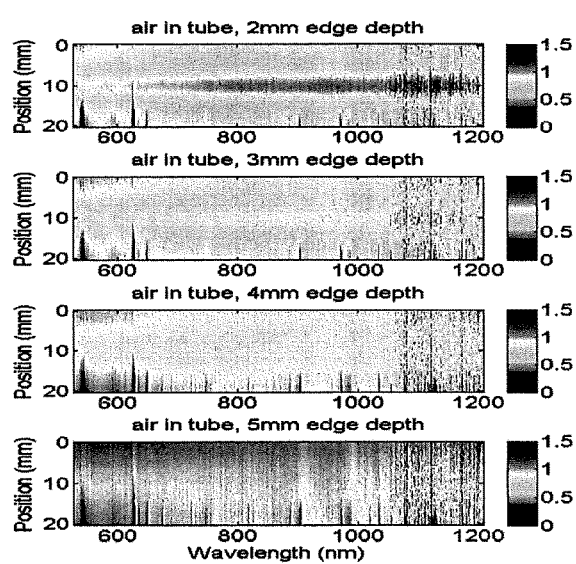
FIG. 7 contains test results from an empty 4 mm tube (air only) at different depths. At each depth, the tube was moved laterally with respect to the probe (position 10 mm corresponds to the tube position directly below the probe).
Figure 11:
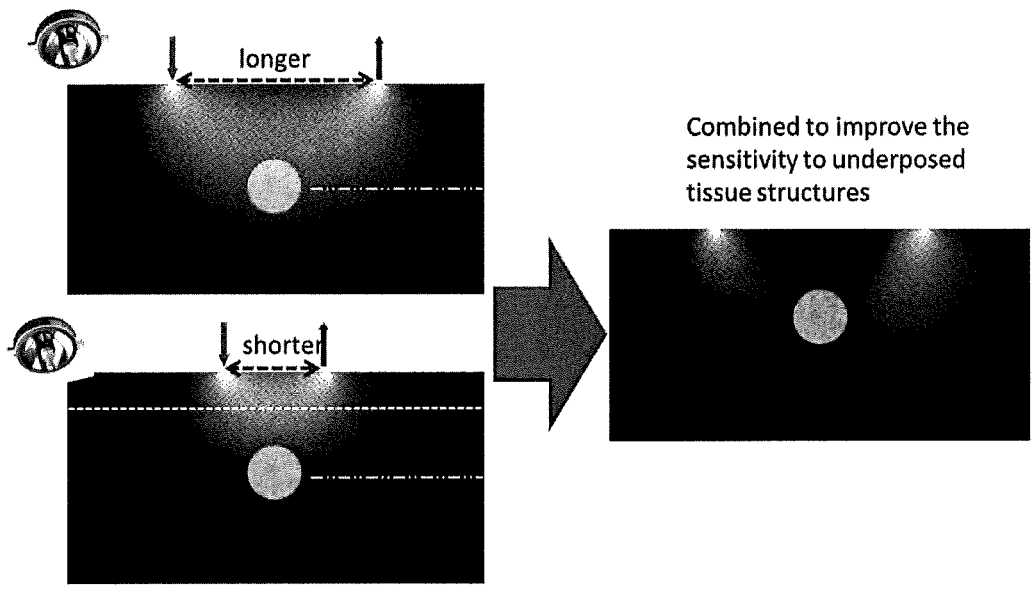
FIG. 11 contains a representation of a site-specific reference for operation under surgical light and suppressing artifacts by the superficial tissue.

FIG. 7 contains test results where the hidden structure was again a tube of 4 mm size. However, in this case the tube was filled with air in each case and the edge depth was varied from 2 mm to 5 mm. As before, the tube was moved laterally with respect to the probe (position 10 mm corresponds to the tube position directly below the probe). As expected, the more deeply situated structure is more difficult to detect than was the case with the more shallow situated tube in FIG. 6.

Figure 8:
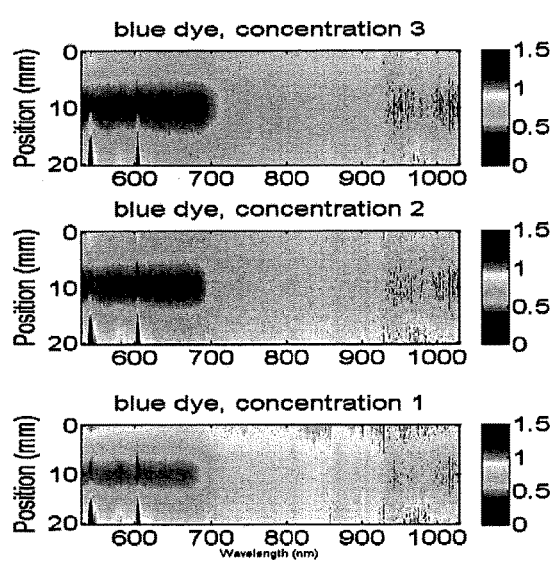
FIG. 8 contains an example of test results of a tube of 4 mm size with dye of different contraptions at a 5 mm edge depth. The tube was moved laterally with respect to the probe (position 10 mm corresponds to the tube position directly below the probe).

FIG. 8 illustrates test results from an embodiment with a tube of 4 mm size and with a dye of a different concentrations, with the tube situated at an edge depth of 5 mm. As before, the tube was moved laterally with respect to the probe (position 10 mm corresponds to the tube position directly below the probe). As expected, higher dye concentrations are more readily detectable.

Figure 9:
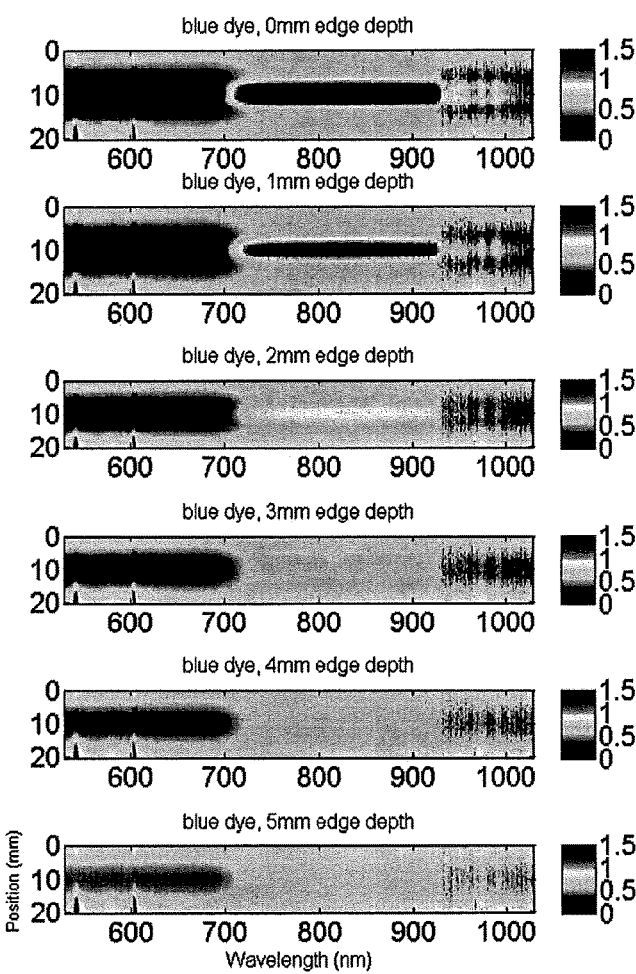
FIG. 9 contains exemplary test results of a tube of 4 mm size with dye of a given concentration at various depths. At each depth, the tube was moved laterally with respect to the probe (position 10 mm corresponds to the tube position directly below the probe). Operated by compensating room light as a demonstration of operating under surgical light.

FIG. 9 contains an illustration of exemplary test results using a tube of 4 mm and blue dye at various edge depths from 0 mm to 5 mm. As might be expected, the frequency change in response to the proximity of the target was more apparent at shallower depths. Further, this particular example was conducted in the presence of ambient room light as a demonstration of the feasibility of the instant embodiment in the when operating under surgical light. In some embodiments a compensation to the observed frequency intensities might be necessary where the ambient light is very strong as it might be in an operating theater.

Finally, turning to the example of FIG. 10, this example illustrates the sorts of differences in the spectra or wavelengths that would be observed for two different targets sizes at the same depth. The changes in the spectrum are caused by the interaction of the object with the light-path. In the case of an artery, the spectral change corresponds to the light absorption by the oxygenated hemoglobin. In the case of a vein, the spectral change corresponds to the light absorption by the de-oxygenated hemoglobin.

As before, in FIG. 10 each strip chart has light wavelength on its horizontal axis and the relative position of the hidden target in its vertical axis, with "12" being centered directly below the probe. This figures illustrates the relative position changes of the tube with respect to the probe, and the different tube sizes.

Different Information for Visualizing Using DOSi

According to an embodiment, in addition to the approach illustrated above other variations are certainly possible. As noted previously, the instant approach utilized changes in the frequency spectrum of diffused light in order to identify subsurface structures. The instant approach is intended to be dynamic with the spectrum of the detected light being calculated and displayed in real time to assist the surgeon in locating structures before making an incision. The instant approach has demonstrated that heterogeneity below the tissue plane is visible in the spectrum of the detected light. Of course, other variations of the teachings herein might be utilized including, for example, using the derivative of the spectral profile ($1^{st}$ order, $2^{nd}$ order, or higher order by taking the respective derivation of the signal with respect to the wavelength) as an alternative o, or possibly used in conjunction with, the spectral calculation illustrated above. Further, other tissue specific information such as chromophore contents that might contribute to the spectral profile might be incorporated into the instant approach by model-fit of the spectral composition of the chromophores. These are just a few of the many possible alternatives ways that the instant teaches might prove to be useful in practice.

If each profile is obtained at different lateral position over the tissue due to freehand or autonomous movement of the probe, an embodiment of the DOSi image can be used to resolve the lateral position of an underlying tissue structure that has a different spectral feature (absorption, scattering, laser induced fluorescence, autofluorescence, etc.).

If each profile is obtained at the same position over the tissue without movement of the probe, one variation of the DOSi image resolves the temporal changes of the underlying tissue structure that has dynamic spectral features (absorption, scattering, laser induced fluorescence, autofluorescence, etc.) due to physiology such as liquid circulation or drug diffusion.

Method of Working Under Surgical Light

According to an embodiment, there is provided an applicator-probe that has three or more fiber channels to form two or more source-detector pairs that share the source channel. In this embodiment, the source-detector pair with shorter source-detector separation will sample the superficial tissue under a local light illuminated by the device at the source fiber position only and under the room surgical light. The source-detector pair with a greater source-detector separation will sample both the superficial tissue and the hidden anatomic structures of interest, under a local device light illuminated at the source fiber position only and under the room surgical light. The spectrum obtained by the source-detector pair with shorter source-detector separation is used as a reference to the spectrum obtained by the source-detector pair with longer source-detector separation to remove the artifacts due to the room surgical light and suppress the effect of the superficial tissues for isolating the spectral changes due to hidden vessels when operating under room surgical light.

Some Exemplary Device Combinations:

Among the many variations that might be used in connection with embodiments disclosed herein include DOSi plus one or a combination of other visualization methods including but not limited to Optical Coherence Tomography and en-face diffuse optical topography, DOSi plus light-based tissue cutting device, and, DOSi plus one or a combination of other visualization methods including but not limited to Optical Coherence Tomography and en-face diffuse optical topography plus light-based tissue cutting device Note that various embodiments differ from prior art devices in that, first, the physical device works with existing surgical instrument, which may be different. The tissue contacting members (i.e., the probes whether they are fiber or optics) in prior art devices are physically integrated with (built into) a tissue manipulating (cutting, grasping, etc.) device which makes them one instrument that is not separable (though the entire instrument can be disposable). By way of comparison, an embodiment of the inventive probe is "piggy-backed" to an existing surgical instrument without making any changes to the surgical instrument itself. This probe can be removed from and attached back to the surgical instrument in a matter of seconds.

Some prior art references use a light-emitting component built into the probe in contact with tissue to produce light by sending an electrical current from a device outside body to the component, and photo-detector component built into the probe in contact with tissue to convert light obtained from tissue to electrical current for transmitting to a device outside body. Another difference between embodiments of the instant disclosure and the prior art is that in various embodiments disclosed herein light is delivered to the probe from a device outside body by using optical fiber without or with other optical components, and the light collected from tissue is delivered from the probe to the device outside the body by using optical fiber without or with other optical components. The cables connecting the probe to the device outside the body conducts light, not electrical current as the specific prior art does.

Some prior art approaches focus on the pulsatile nature of artery blood causing light periodic attenuation of light for detecting artery (what is desired to be detected). The embodiments taught herein do not depend upon the blood pulsation but might be used to detect it as explained previously. The embodiments taught herein uses the static attenuation of the light for detecting vessel structures that do not produce periodical attenuation of light due to blood circulation. Certain prior art approaches use an array of source-detector positions to identify the presence of an underlying artery. The embodiment taught here use only one source-detector position to identify the presence of artery or vein or other structures using the spectral signature.

Another distinction of some embodiments as compared with the prior art is the method used to combine the dynamic tissue spectral information obtained by using broadband light to form an image that visualizes the hidden structure. The dynamic DOS profiles are displayed in the following way or any variation of which, to constitute a two-dimensional image. One dimension of the image represents the wavelength of the spectrum acquired and the other dimension represents the time when the spectrum is acquired. Thus, in this variation the value at one pixel corresponding to specific wavelength and a specific time is the intensity of the spectrum or any parameter originating from the spectral profile. Using this approach the probe may be moved freehand across the surface of the tissue and stopped when the changes in frequency indicates a structure below the surface that is of interest.

When the probe that houses the source and detector is stationary, the resulting two-dimension image represents changes in the DOS spectrum at that position over time. When profiles are acquired at multiple positions by moving the applicator probe manually (e.g., freehand movement) or autonomously, the resulted two-dimension image is a time-series-spatially-resolved spectrogram. By displaying the profiles as a time-series-spatially-resolved spectrogram concurrent with movement (freehand or autonomous or variations of both) of the probe over the tissue area of interest, the dynamic change of the DOS intensity due to underlying anatomic structures can indicate the presence of those structures below the plane of tissue on which the applicator probe is placed.

Further, when the underlying structures contain one artery and one vein in close proximity to each other, there will be a unique pattern of gradient changes of the DOS signals when the applicator probe moves over from the artery to the vein or from the vein to the artery. This unique patterns of signal change can identify a hidden artery and vein complex.

The acquired spectral profiles can be displayed as is indicated above. Alternatively, a three-dimensional image may be constructed where one dimension of the image represents the wavelength of the spectrum acquired, another dimension represents the time when the spectrum is acquired, and the third dimension represents a parameter that is different from the two other dimensions but provides more tissue-specific information, such as fluorescence.

This approach (and its derivatives) of displaying the data (spectral or spectral in combination with other derived information) that has been generated in real-time and preferably acquired using a probe that is piggy-backed to (not physically combined into one piece with) the surgical device, to identify important underlying tissue structures is utilized in some embodiments.

The DOSi studies in porcine models were demonstrated under general room-light. To enable DOSi operation under surgical light, a new applicator-probe with three or more fiber channels to form two or more source-detector pairs with different sampling depths will be utilized. One source-detector pair will have a long (such as 10 mm) source-detector separation for sampling hidden vessel under the surgical light, and the other source-detector pair with short (such as 1 mm) source-detector separation will sample the superficial tissue for site-specific spectral baseline under the surgical light. The source-detector pair with shorter source-detector separation will sample the superficial tissue under a local light illuminated at the source fiber position only and under the room surgical light. The source-detector pair with longer source-detector separation will sample both the superficial tissue and the hidden anatomic structures of interest, under a local device-light illuminated at the source fiber position only and under the room surgical light. The spectrum obtained by the source-detector pair of shorter source-detector separation is used as a reference to the spectrum obtained by the source-detector pair of longer source-detector separation to remove the artifacts due to the room surgical light and suppress the effect of the superficial tissues for isolating the spectral changes due to hidden vessels when operating under surgical light The DOSi system can integrate a second spectrometer for dynamic and site-specific referencing using the shorter-distance source-detector pair. For example, the room surgical light could be acquired using one set of detectors, since it is all over the tissue surface, so its effect on the signal is superficial and could be picked up a the smaller source-detector pair. The ambient lighting becomes a noise relative to the signal obtained from the tissue deeper, and can be removed from the signals obtained by the longer source-detector pair for cleaner probing of deeper tissue under room surgical lighting. If an ultra-bright broadband light source is used it could be gated when operating under surgical-light in order to reduce its impact. The DOSi displays each new line of corrected DOS profile by scrolling in to an image with previously displayed profile up to a certain number of profiles, producing the time-series-spatially-resolved DOS changes as an image.

There is provided herein a novel laparoscopic visualization instrument to intraoperatively augment surgeon knowledge about hidden important anatomic structures such as major artery and vein complex. Preventing iatrogenic injuries to major vasculature is challenging in minimally invasive procedures, particularly when performing on obese patients, due to limitations in the surgeon's ability to visualize those anatomic structures hidden below the fat to navigate around them.

A new visualization technology embodiment has been demonstrated, scanning diffuse optical spectroscopy imaging (DOSi), which has shown to augment surgeon knowledge of hidden major artery-vein complex during referenced open-surgery tests. Scanning DOSi is a diffuse optical spectroscopy technology that uses distantly placed source and detector to interrogate the underlying tissue structures such as artery and vein complex hidden in a few millimeters below the fatty plane undergoing dissection. The underlying tissue structures such as artery and vein complex is identified by the strong or spectrally-distinguished absorptions of the light across visible and near-infrared spectrum) by respectively the highly oxygenated arterial blood and more deoxygenated venous blood.

One aspect that makes the instant approach attractive is that the use of scanning DOSi makes possible visualizing hidden anatomic structures such as artery and vein complex is that it forms an image of subsurface tissue attenuation spectrum during scanning (freehand or autonomous) of the applicator-probe over the tissue area of interest.

This new scanning DOSi technology using an applicator probe compatible with existing minimally invasive surgical instrument has been preliminarily tested in porcine models in vivo. The applicator-probe sleeves on to the existing tissue-maneuvering instrument, and moves in-contact with the tissue for intraoperative vessel identification or moves away from the tissue for proceeding with dissection, by simple sliding of the probe along the stem of the tissue maneuvering instrument.

According to one embodiment, the applicator-probe contains a pair of source-detector fiber channels separated 10 mm apart that in laboratory testing has identified a 4 mm diameter tube filled with 33% red dye, 33% yellow dye, 33% green dye, embedded in a slab of greater than 2 mm thick avian muscle tissue. A laser-driven broad-band light source enables in vivo testing in a 100-300 ms data acquisition speed/sample rate. The tests were done in pigs in an open-surgery platform to ensure experimental reference of the vasculature. In seven individual tests performed on 4 pigs in vivo by three different surgeons, a prototype scanning DOSi instrument successfully identified the aorta-vena complex covered with 2~4 mm of fat layer, under the general lighting in the OR with the surgical lighting turned away.

Turning to another application of the instant technology, there is a need for rapid, non-invasive methodologies to accurately evaluate organ quality for procurement and this is especially true in the context of liver transplantation due to the shortage of donor organ and increased proportion of donor organ of marginal quality. Currently, pathology of deceased liver donors is determined by gross examination by a surgeon and occasionally there will be analysis of histopathology performed by a pathologist. Histopathology is not always performed due to time constraints and invasiveness, among other issues. The cryosection histology as the standard of pre-transplantation donor liver assessment also has concerns of artifacts and sampling errors. The lack of assessment of the underlying pathology of a deceased liver donor could significantly affect the liver graft success. In an effort to meet these challenges, we have tested diffuse optical spectroscopy imaging (DOSi) for testing the potential of non-invasive\non-destructive evaluation of liver pathology.

Turning first to the example of FIG. 3, FIG. 3A contains a tissue-specific raw DOS spectral profile. FIG. 3B contains a graphic that includes the profiles of FIG. 3A that have been normalized against a baseline profile. The resulted relative spectral profile amplifies spectral changes caused by pathology relative to a normal liver as is indicated in FIG. 3C. The profile results in FIG. 3B have been separated and displayed as an image in FIG. 3C. The intensity in each bar in FIG. 3C indicates the magnitude of the deviation of that spectral profile from the baseline. The more intense the deviation is, the greater the deviation of that curve from the baseline which tends to indicate a potentially higher pathology in the tested liver. It should be noted that some embodiments use color instead of grey-scale intensity in order to highlight deviations from the baseline.

Probing a tissue structure by using optical spectrum of any kind is inevitably affected by the tissue heterogeneity above the structure. For probing any tissue structure, such as a solid organ, the capsule that is a thin but highly scattering collagen-rich layer confounds the optical spectral measurements. Accurate and sensitive probing of the tissue enclosed by the capsule requires knowing what the capsule does to the probing. The capsular optical properties and thickness combined are believed to affect how accurate the diffuse reflectance on the surface of a capsular solid organ represents that on the sub-capsular parenchyma. Monte Carlo ("MC") simulations on two-layer geometries have been used to evaluation how a thin superficial layer with the thickness from 10 μm to 1000 μm affected the surface diffuse reflectance over a source-detector-separation spanning 0.01 mm to 10 mm. The simulations represented the superficial layer presenting various contrasts concerning refractive index, anisotropy factor, absorption coefficient, and reduced scattering coefficient, versus those of the sub-surface main medium. An analytical approach modeled the effects of the superficial layer of various thicknesses and optical properties on diffuse reflectance. Diffuse reflectance spectroscopy was performed ex vivo on 10 fresh human livers and 9 fresh human kidneys using a surface probe with a 3-mm source-detector-separation. The difference of the device-specific diffuse reflectance on the organ between the "with the capsule" and "without the capsule" samples has significantly greater spectral variation in kidney than in liver. The significantly greater spectral deviation of surface diffuse reflectance between with and without the capsule in kidney than in liver was analytically accountable by considering the much thicker capsule of the kidney than of the liver.

Figure 5:
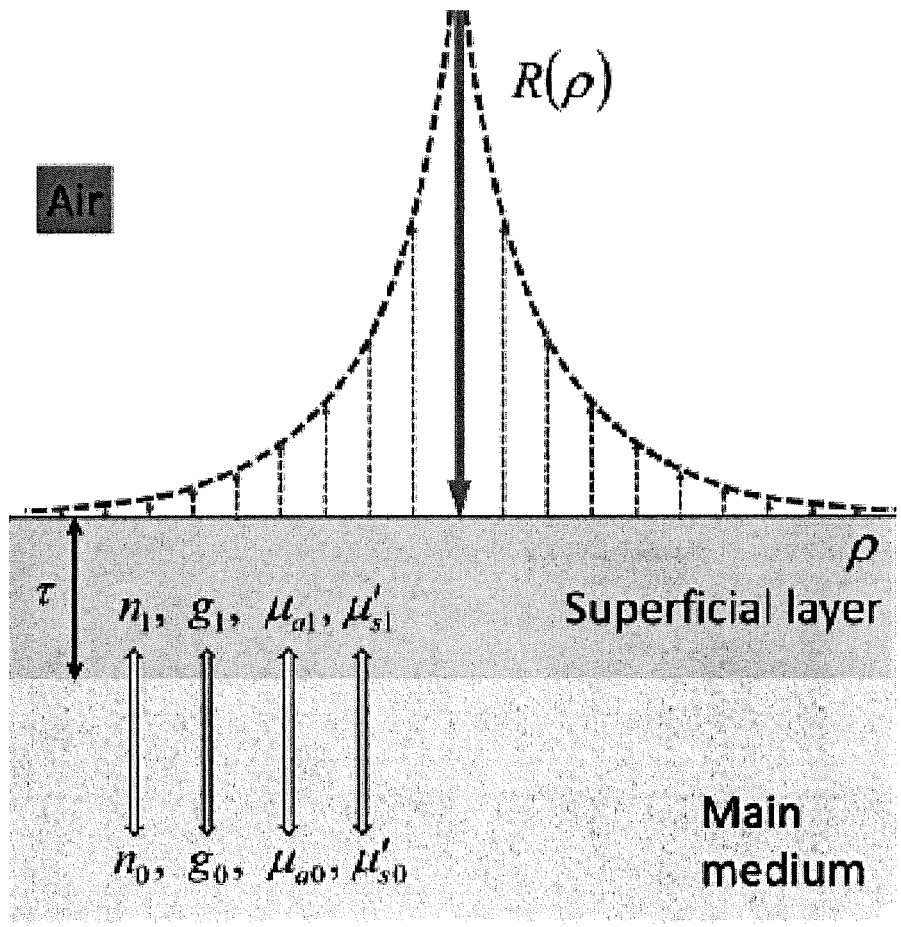
FIG. 5 contains an illustrative medium geometry of that was used in a Monte Carlo simulation of an embodiment.

MC simulations were used to evaluate how the optical contrast of a thin (less than 1000 μm thick) superficial layer with respect to the sub-surface main medium would affect the spatially resolved diffuse reflectance measured on the surface of the superficial layer. The medium geometry of the MC simulation is depicted in FIG. 5. A planar 2-layer medium geometry was implemented for evaluating the diffuse reflectance R(ρ) measured at a lateral distance p from the point of light injection into the medium. A set of optical properties including the refractive index n, the anisotropy factor g, the absorption coefficient $\mu_a$, and the reduced scattering coefficient $\mu'_s$ were assigned independently to the superficial layer and the main medium. These four optical properties were used as the primary parameters for each of the two layers. The parameters associated with the main medium are marked by a subscript of "0", and those with the superficial layer by a subscript of "1".

Each MC simulation corresponded to the superficial layer differing from the main medium in only one of the four primary parameters including $n_1$, $g_1$, $\mu_{a1}$, and $\mu'_{s1}$. Two stages of MC simulations were performed. The first stage of MC simulations evaluated the effect of each of the four primary parameters of the superficial layer at a fixed setting of the main medium parameters on the diffuse reflectance for a superficial layer thickness ranging from 10 μm to 1000 μm. The individual patterns revealed by the first stage MC simulations, which constituted 94.9% of the total number of simulations, regarding how each of the four capsular contrasts over the main medium affected the diffuse reflectance were used to gauge the analytical model development. As will be shown from the first-stage of the MC simulations conducted for a fixed setting of the main medium properties, the diffuse reflectance from the two-layer geometry with a thin superficial layer (≤1000 μm thick) is not sensitive to $n_1$ and $g_1$ (or equivalently the contrast of each over its main medium counterpart) over their respective ranges covering more than what a biological tissue will present. These outcomes were used to constrain the parameter setting in the next stage of MC simulation that was intended for evaluating the effect of the change of main medium properties on diffuse reflectance in a more pathologically relevant parameter setting of the superficial layer. The subsequent stage of MC simulations thus was performed at the absence of a superficial layer contrast on the refractive index or anisotropy factor over the main medium. In consideration of the high scattering of organ capsule due to collagen content, and a liver capsule being approximately 10 μm thick and a kidney capsule being approximately 200 μm thick, the superficial layer in the second stage of MC simulations was thus fixed at a high scattering property with the thicknesses of 10 μm and 200 μm only, whilst the $\mu_{a0}$ and $\mu'_{s0}$ of the main medium were changed to evaluate how much the main medium property would affect the spatially resolved surface diffuse reflectance at a fixed setting of a highly scattering superficial layer.

By way of summary, the above-described Monte Carlo and empirical results indicate that capsular optical properties and thickness combined affect how accurate the diffuse reflectance on the surface of a capsular solid organ represents that on the sub-capsular parenchyma. The projection of the combined effect of the contrast of the optical properties over the main medium and the thickness of the capsular layer is supported by Monte Carlo simulations and modeled by an analytical method. The Monte Carlo simulations are implemented for two-layer geometries containing a thin superficial layer with the thickness from 10 μm to 1 mm to evaluate the surface diffuse reflectance over a source-detector-separation spanning 10 μm to 10 mm. The superficial layer was set to have various contrasts concerning refractive index, anisotropy factor, absorption coefficient, and reduced scattering coefficient, versus those of the sub-surface main medium. A novel analytical approach by modifying a master-slave dual-source setting to a master-slave-differential triple-source configuration was proposed to account for how the superficial layer of various thicknesses and optical properties affect surface diffuse reflectance. Diffuse reflectance spectroscopy were also performed ex vivo on 10 fresh human livers and 9 fresh human kidneys. The device-specific diffuse reflectance performed on the capsular surface was as high as 170% of that on the sub-capsular parenchyma in kidney. The device-specific diffuse reflectance performed on the capsular surface was as high as 120% of that on the cross-sectional parenchyma in liver. According to the analytical model, the significantly greater spectral deviation of surface diffuse reflectance between with and without capsule in kidney than in liver was related to the much thicker capsule of the kidney than the liver. Knowing the effect of the capsule on DOS of tissue enclosed by the capsule allows developing a model for compensating the effect of the capsule on DOS such that the DOS signals caused by only the tissue enclosed by the capsule be identified for sensitive imaging/sensing/identification of tissue structures in the presence of confounding anatomic layers. Other variations of the approach taught herein include developing an applicator-probe integrating spectra-reference channel to enhance fDOSi operation under surgical light, upgrading the instrument engine for real-time fDOSi image-formation under surgical lighting, and, testing the robotic operation of fDOSi for blinded and referenced identification of fat-covered aorta-vena cava and renal artery-vein complex.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. An applicator probe for visualizing an interior of a tissue having a planar surface, comprising:
   (a) a laparoscopic probe, said probe having a probe shaft that terminates in a pair of probe jaws, said probe jaws at least for grasping the tissue when said probe jaws are closed together;
   (b) a hollow tube sleeved onto said probe shaft,
      said tube having a proximal end and a distal end,
      said tube having a diameter sufficient
         to allow said probe shaft to be slidable within an interior of said tube and
         to allow said probe jaws to be extended from and retracted into said tube proximal end when said jaws are closed together;
   (c) a left extruded terminal extending parallel to said tube from a left side of said proximal end of said tube;
   (d) a right extruded terminal extending parallel to said tube from a right side of said proximal end of said tube, said right extruded terminal coterminous with said left extruded terminal and spaced apart therefrom a distance sufficient to allow said probe jaws to be extended from said tube and retracted into said tube therebetween;
   (e) a left longitudinal groove continuously extending laterally along a left external side of said tube from a left side of said distal end of said tube to a terminus of said left extruded terminal;
   (f) a right longitudinal groove continuously extending laterally along a right external side of said tube from a right side of said distal end of said tube to a terminus of said right extruded terminal;
   (g) at least one source optical fiber sized to fit within said left longitudinal groove and extending within it along a left side of said tube from said left side of said distal end of said tube to said terminus of said left extruded terminal, each of said at least one source optical fiber being adapted to receive light from a light source at a first source end and emit said light at a second source end proximate to said terminus of said left extruded terminal; and
   (h) at least one detector optical fiber coterminous with said source optical fiber and sized to fit within said right longitudinal groove and extending within it along said right side of said tube from a right side of said distal end of said tube to said terminus of said right extruded terminal, each of said at least one detector optical fiber being adapted to receive diffuse light through the tissue at a second receiving end proximate to said terminus of said right extruded terminal from light emitted from said second source end of said at least one source optical fiber end and emit said received diffuse light from a first receiving end of said at least one detector optical fiber when said left and right extruded terminals are simultaneously placed into contact with the tissue and the light source is activated.

2. The applicator probe according to claim 1, wherein said light source comprises a plurality of light source units.

3. The applicator probe according to claim 1, wherein said light source is a laser-driven broad band light source.

4. The applicator probe according to claim 1, wherein said at least one source optical fiber first end and said at least one detector optical fiber first end are between 1 mm and 10 mm apart.

5. The applicator probe according to claim 1, wherein said tube is sized to sleeve onto an 8 mm shaft of a robotic-assisted tissue manipulating instrument or a laparoscopically compatible device.

6. The applicator probe according to claim 1, wherein said at least one source optical fiber comprises a single optical fiber and said at least one detector optical fiber comprises a single optical fiber.

7. The applicator probe according to claim 1, wherein the light source transmits light at wavelengths between 300 nm and 1000 nm.

8. The applicator probe according to claim 1, further comprising:
a spectrometer in optical communication with each of said detector fiber first end.

9. The applicator probe according to claim 8, wherein said spectrometer comprises a desktop computer, a laptop computer, a smart phone, or a tablet computer.

10. An applicator probe for visualizing an interior of a tissue having a planar surface, comprising:
(a) a laparoscopic probe, said probe comprising a probe shaft terminating in a pair of probe jaws, said probe jaws being operable to grasp the tissue when closed together and release it when opened apart;
(b) a cylindrical body slidably sleeved onto said laparoscopic probe shaft, said body terminating at an open first end in a pair of coterminous equal length spaced apart left and right extruded terminals, said left extruded terminal extending parallel to said body from a left side of said body and said right extruded terminal extending parallel to said body from a right side of said body,
said body having a diameter sufficient to allow said probe jaws to be extended from and retracted into said body between said extruded terminals when said probe jaws are closed together;
(c) a left longitudinal groove extending from a body second end along a left side of said body to a terminus of said left extruded terminal;
(d) a right longitudinal groove extending along a right side of said body from said body second end to a terminus of said right extruded terminal;
(e) at least one source optical fiber, each of said at last one source optical fiber sized to fit within said left longitudinal groove and extending within it along a left side of said body from a left side of said body second end to said terminus of said left extruded terminal, each of said at least one source optical fiber adapted to receive light from a light source at a first source end and emit light therefrom at a second source end proximate to said terminus of said left extruded terminal; and
(f) at least one detector optical fiber, each of said at least one detector optical fiber having a second end coterminous with each of said at least one source optical fiber second end and sized to fit within said right longitudinal groove and extending within it along a right side of said body from a right side of said body second end to said terminus of said right extruded terminal, each of said detector optical fiber second end adapted to receive diffuse light through the tissue emitted from said at least one o source optical fiber second end and transmit said received diffuse light to a first detector end when said left and right extruded terminals are placed into contact with the tissue and the light source is activated.

11. The applicator probe according to claim 10, wherein said light source comprises a plurality of light source units.

12. The applicator probe according to claim 10, wherein said light source is a laser-driven broad band light source.

13. The applicator probe according to claim 10, wherein said at least one source optical fiber first end and said at least one detector optical fiber first end are between 1 mm and 10 mm apart.

14. The applicator probe according to claim 10, wherein said body is sized to sleeve onto an 8 mm shaft of a robotic-assisted tissue manipulating instrument or a laparoscopically compatible device.

15. The applicator probe according to claim 10, wherein said at least one source optical fiber comprises a single optical fiber and said at least one detector optical fiber comprises a single optical fiber.

16. The applicator probe according to claim 10, wherein the light source transmits light at wavelengths between 300 nm and 1000 nm.

17. The applicator probe according to claim 10, further comprising:
(g) a spectrometer in optical communication with each of said detector optical fiber first end.

18. The applicator probe according to claim 17, wherein said spectrometer comprises a desktop computer, a laptop computer, a smart phone, or a tablet computer.

\* \* \* \* \*